(12) United States Patent
Hafeli et al.

(10) Patent No.: US 6,413,271 B1
(45) Date of Patent: Jul. 2, 2002

(54) METHOD OF MAKING A RADIOACTIVE STENT

(75) Inventors: Urs Hafeli, Cleveland; Uziel Landau, Shaker Heights; Matt C. Warburton, Strongsville, all of OH (US)

(73) Assignees: The Cleveland Clinic Foundation; Case Western Reserve University, both of Cleveland, OH (US)

( * ) Notice: Subject to any disclaimer, the term of this patent is extended or adjusted under 35 U.S.C. 154(b) by 0 days.

(21) Appl. No.: 09/481,247

(22) Filed: Jan. 11, 2000

Related U.S. Application Data

(62) Division of application No. 09/019,908, filed on Feb. 6, 1998, now Pat. No. 6,077,413.

(51) Int. Cl.$^7$ ................................................ A61F 2/06
(52) U.S. Cl. ...................... 623/1.15; 623/1.44; 623/1.46
(58) Field of Search .................. 623/1.1, 1.11, 623/1.15, 1.46, 1.45, 1.44; 600/3, 8, 7, 1, 12; 606/108, 155, 191, 192, 194; 608/195

(56) References Cited

U.S. PATENT DOCUMENTS

| | | | |
|---|---|---|---|
| 4,197,170 A | | 4/1980 | Malson et al. |
| 5,059,166 A | | 10/1991 | Fischell et al. |
| 5,176,617 A | | 1/1993 | Fischell et al. |
| 5,213,561 A | | 5/1993 | Weinstein et al. |
| 5,354,257 A | | 10/1994 | Roubin et al. |
| 5,411,466 A | | 5/1995 | Hess |
| 5,605,530 A | | 2/1997 | Fischell et al. |
| 6,010,445 A | * | 1/2000 | Armini ............................ 600/3 |
| 6,045,495 A | * | 4/2000 | Weiberger ....................... 600/3 |

OTHER PUBLICATIONS

"Rhenium Plating", by Fink, et al., Sixty–sixth General Meeting, New York City, Sep. 29, 1934, pp. 471–475.
"Plating Rhenium and Rhenium–Nickel Alloys", by Young, *Metal Industry*, May, 1936, vol. 34, pp. 176–177.
"Electrodeposition of Rhenium from Aqueous Solutions", by Netherton, et al., Jun., 1949, pp. 324–328.
"Electrodeposition of Rhenium–Cobalt and Rhenium–Iron Alloys", by Netherton, et al., *Journal of the Electrochemical society*, Feb. 1952, pp. 44–47.
"Electroplating of Rhenium", by Root, et al., 1962, pp. 181–188.
"Recent Developments in the Application and Electroplating of Rhenium", by Camp, May, 1975, pp. 413–416.
"Low–Dose β–Particle Emission from 'Stent' Wire Results in Complete, Localized Inhibition of Smooth Muscle Cell Proliferation", by Fischell, et al., *Circulation*, vol. 90, No. 6, Dec., 1994, pp.2956–2963.
"Low–Dose Radioactive Endovascular Stents Prevent Smooth Muscle Cell Proliferation and Neointimal Hyperplasia in Rabbits", by Hehrlein, et al., *Circulation*, vol. 92, No. 6, Sep. 15, 1995, pp. 1571–1575.

"Experimental Results with Endovascular Irradiation Via a Radioactive Stent", by Carter, et al., *Int. J. Radiation Oncology Biol. Phys.*, vol. 36, No. 4, 1996, pp. 797–803.
"Effects of Endovascular Radiation from a β–Particle–Emitting Stent in a Porcine Coronary Restenosis Model", by Carter, et al., *Circulation*, vol. 94, No. 10, Nov. 15, 1996, pp. 2364–2368.
"Pure β–Particle–Emitting Stents Inhibit Neointima Formation in Rabbits", by Hehrlein, et al., *Circulation*, vol. 93, No. 4, Feb. 15, 1996, pp. 641–645.
"A Novel Brachyehtapy Source for Treatment of Coronary Artery Restenosis", by Li, et al., 1996, pp. 67–72.

* cited by examiner

*Primary Examiner*—Michael J. Milano
*Assistant Examiner*—Vy Q. Bui
(74) *Attorney, Agent, or Firm*—Calfee, Halter & Griswold LLP

(57) ABSTRACT

The present invention provides a method for preparing an implantable, medical device having at least one radioactive metallic surface. The method comprises the steps of depositing a radioactive metal layer onto the surface of the device. The metal layer comprises a radioactive metal that emits beta particles and that has a half-life of between 2 hours and 7 days and a maximum beta energy of between 0.7 and 2.3 MeV. In one embodiment, the radioactive layer is deposited by electroplating the radioactive metal and a carrier metal onto the metallic surface. In another embodiment, the method further comprises the step of electroplating a second metallic layer comprising a barrier metal onto the radioactive metal layer. The present invention also provides an implantable medical device comprising a surface having a metallic surface comprising a radioactive metallic coating thereon. The coating comprises a radioactive layer comprising a radioactive metal that emits beta-particles. The radioactive metal has a half-life of between 2 hours and 7 days and an energy level of from about 0.7 MeV to 2.3 MeV. In one embodiment the radioactive layer further comprises a carrier metal. In another embodiment, the coating further comprises a second layer deposited on the radioactive layer. The second layer comprises a biocompatible metal. In a preferred embodiment the medical device is a stent. The present invention also relates to a system for applying the radioactive coating to the implantable medical device. The system comprises a package and a sterile electroplating cell contained within the package. The electroplating cell comprises a wall defining a chamber and an electrode attached to the inside wall of the cell or embedded in the inside wall of the cell, so that at least a portion of the electrode is in communication with the chamber. The system further comprises a conductive fastener for electrically connecting the metallic medical device to the power supply and positioning the device within the chamber.

22 Claims, No Drawings

METHOD OF MAKING A RADIOACTIVE STENT

This application is a divisional of the commonly assigned, U.S. patent application Ser. No. 09/019,908, filed Feb. 6, 1998, now issued as U.S. Pat. No. 6,077,413.

BACKGROUND OF THE INVENTION

The present invention relates to a method of preparing an implantable radioactive metallic medical device. More particularly, the present invention relates to a method of preparing a radioactive metallic stent for use in preventing restenosis in atherosclerotic coronary arteries that have been subjected to percutaneous transluminal coronary angioplasty, hereinafter referred to as "balloon angioplasty".

Atherosclerosis is a disease in which vascular lesions or plaques consisting of cholesterol crystals, necrotic cells, excess fiber elements and calcium deposits accumulate on the interior walls of an individual's arteries. The presence of such plaques in the artery leads to thickening and retraction of the artery. Eventually the enlargement of such plaques can lead to an occlusion of the lumen of the artery at the site of the lesion. One of the most successful procedures for treating the narrowing of the arteries caused by atherosclerosis is balloon angioplasty. Balloon angioplasty consists of introducing a deflated balloon into the atherosclerotic artery, placing the balloon adjacent the site of the plaque or atherosclerotic lesion, inflating the balloon to a pressure of approximately 6 to 20 atmospheres thereby "cracking" the plaque and increasing the cross-sectional area of the lumen of the artery.

Unfortunately, the pressure that is exerted on the plaque during balloon angioplasty also traumatizes the artery. Accordingly, in 30–40% of the cases the vessel either gradually renarrows or recloses at the locus of the original stenotic lesion. This gradual renarrowing or reclosure is referred to as restenosis. Studies of the mechanism of restenosis have shown that it is due in part to a proliferation of smooth muscle cells and in part to retraction or recoil of the blood vessels.

A number of approaches for preventing restenosis are currently being used or tested. One approach employs a metallic stent which is deployed at the site of the stenotic lesion following balloon angioplasty. Typically, metallic stents are made in the form of a mesh-like network of linked wires and open spaces. Metallic stents have the mechanical strength necessary to prevent recoil or retraction of the barotraumatized vessel. However, the metallic stents that are presently used do not prevent proliferation of the smooth muscle cells.

Animal studies have shown that the rate of restenosis can be further reduced by implanting radioactive metallic stents at the site of the atherosclerotic lesion following balloon angioplasty. The local irradiation supplied by such stents prevents smooth muscle cell proliferation. The use of such radioactive stents is currently being tested in a clinical phase I trial. The stents that are being used in these trials are loaded with $^{32}$P by ion implantation. This process involves the bombardment of rotating stents with $^{32}$P ions. The $^{32}$P ions become embedded in the metal surface to a depth of a few $\mu$m.

Typically, $^{32}$P stents cannot be activated within the hospital. $^{32}$P stents must be activated in advance and then shipped to the hospital. Because of constant decay of the radioisotope, $^{32}$P stents may not be able to deliver the required dose to the site of the stenotic lesion if stored for any length of time at the hospital. Therefore, unless a hospital receives a fresh supply of $^{32}$P stents of various types, lengths and doses on a daily basis, a $^{32}$P stent that matches the individual lesion characteristics of the patient may not be available at the time of insertion. In addition, $^{32}$P stents deliver radiation to the area near the stent for more than 30 days after implantation. Radiobiological concerns make delivering the radiation over this length of time undesirable. Previous studies have shown that irradiation of the vessel within a few hours prior to and 3 days post angioplasty is the most desirable range of time for treatment. Thus, the length of time the patient is exposed to radiation from the $^{32}$P stents is excessive. Moreover, it is likely that $^{32}$P stents will deliver radioactivity to the target tissue at a dose rate of less than 10 cGy per hour during most of the time the $^{32}$P stent delivers radioactivity. Concerns have been raised that subjecting the cells in the vicinity of the $^{32}$P stent to such low dose rates of radiation following implantation may not only be ineffective for restenosis prevention, but may even activate cellular proliferation.

Accordingly, it is desirable to have a new radioactive metallic stent and methods of preparing the same that overcome the disadvantages of the $^{32}$P stent. A stent that is loaded with a radioisotope that delivers radiation for a shorter period of time is desirable. A stent that is capable of delivering radioactivity at a dose rate of at least 10 cGy per hour during the first twelve hours to twelve days after the stent is implanted is also desirable. A method which is relatively simple and rapid and allows a predictable amount of radioactivity to be incorporated into stents of various lengths and types on the same day the stenting procedure is being performed is especially desirable.

SUMMARY OF THE INVENTION

The present invention provides a simple and rapid method for preparing an implantable medical device having at least one radioactive metallic surface. The method comprises the steps of depositing a radioactive metal layer onto the surface of the device. The metal layer comprises a radioactive metal that emits beta particles and that has a half-life of between 2 hours and 7 days and a maximum beta energy of between 0.6 and 2.3 MeV. In one embodiment, the radioactive layer is deposited by electroplating the radioactive metal and a carrier metal onto the metallic surface. The carrier metal has the ability to adhere to the metal surface and to co-deposit with the radioactive metal. In another embodiment, the method further comprises the step of electroplating a second metallic layer comprising a barrier metal onto the radioactive metal layer. The barrier metal is biocompatible and has the ability to adhere to the radioactive layer.

The present invention also provides an implantable, radioactive metallic medical device comprising a surface having a radioactive metallic coating thereon. The coating comprises a radioactive layer comprising a radioactive metal that emits beta-particles having a half-life of between 2 hours and 7 days and an energy level of from about 0.6 MeV to 2.3 MeV. In one embodiment the radioactive layer further comprises a carrier metal. In another embodiment, the coating further comprises a second layer deposited on the radioactive layer. The second layer comprises a biocompatible metal. In a preferred embodiment the medical device is a stent.

The present invention also relates to a system for applying the radioactive coating to the implantable medical device. The system comprises a package and a sterile electroplating cell contained within the package. The electroplating cell comprises a wall defining a chamber and an electrode attached to the inside wall of the cell or embedded in the inside wall of the cell, so that at least a portion of the electrode is in communication with the chamber. The system further comprises a conductive fastener for electrically connecting the metallic medical device to the power supply and positioning the device within the chamber. In a preferred embodiment, the cell further comprises an inlet port in fluid communication with the chamber for delivering solutions to the chamber, and an outlet port in communication with the chamber of the cell for removing solutions from the chamber.

DETAILED DESCRIPTION OF THE INVENTION

Method for Making a Radioactive Metallic Medical Device

In one aspect, the present invention provides a method for making radioactive any medical device that comprises at least one surface made from a metal, preferably from a biocompatible metal such as, for example, stainless steel, tantalum, cobalt-based alloys or nitinol. The method comprises depositing a coating which comprises a radioactive metal onto the device. The radioactive metal emits beta particles, and preferably, low energy gamma rays. The radioactive metal has a half-life of between 2 hours and 7 days and a maximum beta energy of between 0.6 and 2.3 MeV. Suitable metals for forming the radioactive layer include, but are not limited to, radioactive rhenium (Re) as $^{186}$Re and $^{188}$Re, either combined or alone; radioactive yttrium (Y) as $^{90}$Y; radioactive holmium (Ho) as $^{166}$Ho, radioactive praseodymium (Pr) as $^{142}$Pr, radioactive lanthanum (La) as $^{140}$La, radioactive dysprosium (Dy) as $^{165}$Dy, radioactive samarium (Sm) as $^{153}$Sm, radioactive copper (Cu) as $^{64}$Cu and $^{67}$Cu, or radioactive gold (Au) as $^{198}$Au, or combinations thereof. All of these radioisotopes emit beta-electrons that are able to penetrate human tissue to a depth desirable for the treatment of restenosis. In addition, all of these radioisotopes, with the exception of $^{90}$Y emit gamma rays in amounts that are too small to be radiotoxic to normal tissue but sufficient to make gamma camera imaging of the implanted device possible. Such imaging allows one to precisely monitor the location of the radioactive device following implantation in the patient.

Preferably, the coating comprises $^{188}$Re. $^{188}$Re is a beta-emitting radioisotope with a half-life of 17 hours and an average tissue penetration of 3 mm. Dosimetric studies have shown that this isotope is able to deliver the necessary dose of 15–20 Gy to the smooth muscle cells in the media and adventitia of an artery while sparing the tissue that is more distant from the lumen than the adventitia. Thus, $^{188}$Re has the ideal treatment range for coronary arteries and other blood vessels, i.e. tissue penetration to a depth of up to 3.5 mm.

The rhenium radioisotope $^{186}$Re in aqueous solution in the form of the highly water-soluble perrhenate is currently available from Oak Ridge National Laboratory, Oak Ridge, Tenn. Alternatively, non-radioactive rhenium compounds such as metallic rhenium, rhenium oxides such as $ReO_2$ and $ReO_3$, and preferably, dirhenium heptoxide, $Re_2O_7$ can be purchased from a number of chemical suppliers and then activated in a nuclear reactor. When placed in aqueous buffer, radioactive $Re_2O_7$ dissociates immediately into the radioactive perrhenate anion, $ReO_4^-$. Finally, pure $^{188}$Re can be made employing a $^{188}$W/$^{188}$Re generator which is currently available from Oak Ridge National Laboratory. The $^{188}$W/$^{188}$Re generator consists of a silica column with the parent nuclide $^{188}$W firmly bound to it. $^{188}$W is a radioisotope that decays with a half-life of 69.4 days into the daughter nuclide $^{188}$Re. Since the radioactive perrhenate is highly water soluble, it is currently possible to pump 10 ml of saline through the silica column daily and to thereby extract pure $^{188}$Re in amounts of up to 37 GBq. The half-life of the parent nuclide $^{188}$W is such that each generator can be used for at least 3 months.

In one embodiment, the radioactive metal is electroplated onto the metal surface in a layer that further comprises a carrier metal. The carrier metal adheres to the metal surface and, preferably, is less noble than the radioactive metal. The carrier metal is cohesive. Thus, the carrier metal is especially desirable when the radioactive metal does not readily adhere to the metal surface or to itself, i.e. the radioactive metal has insufficient cohesiveness to form a continuous metallic layer. The carrier metal also serves to provide greater control over deposition of the radioactive metal onto the metal surface and to provide a continuous metal layer that is more durable. Preferably, the carrier metal is capable of being electroplated with high current efficiency from an aqueous solution. More preferably, the second metal is a biocompatible. Suitable carrier metals include, but are not limited to cobalt, nickel, chromium, manganese, iron, gold and combinations thereof. Because of its good compatibility, water solubility, and its relatively lower standard potential, it is preferred that cobalt, which has a standard potential of –0.280 V, be used as the carrier metal when rhenium, which has a standard potential of +0.368 V, is used as the radioactive metal.

In another embodiment the method comprises a further step of electroplating a second metallic layer comprising a biocompatible barrier metal. The barrier metal is capable of adhering to the radioactive layer and provides a barrier between the radioactive metal and the surrounding tissue and, thus, reduces leakage or release of the radioactive metal from the device. Preferably, the barrier metal is biocompatible. More preferably, the barrier metal is more ductile than the carrier metal and, thus, improves the capability of the medical device to be bent without cracking the radioactive coating. Suitable barrier metals include, but are not limited to, gold and platinum. Because of its good biocompatibility and inertness, it is preferred that gold be used as the barrier metal.

Preferably, before the radioactive layer is electroplated onto the metallic surface, oily contaminants are removed from the metallic surface by immersing in an organic solvent, such as for example acetone, or hexane. To ensure good adherence of the coating to the metal surface, it is also preferred that the surface be treated to remove oxide layers and prepare the device for electroplating of the radioactive layer. A procedure of simultaneously removing the oxide layers and providing a seed or nucleation layer on the metal surface, which is referred to hereinafter as "cathodic striking", may involve immersing the metallic surface or the entire device into a sterile electroplating bath that contains a sterile acidic electrolyte solution comprising ions of the carrier metal. The metallic surface of the device, particularly the stent, is then electrically connected to the negative pole of a power supply and immersed into the electroplating bath and treated using a cathodic strike protocol. Such protocols are within the skill of the art. Generally, cathodic striking involves treatment times of a few minutes or seconds and employs current densities that are far higher, typically ten times higher, than the current densities used in the subsequent electroplating step, i.e. more than 100 and less than 10,000 $A/m^2$.

Immediately following cathodic striking of the metallic surface, the metallic surface or the entire device is immersed in a sterile electroplating bath which contains a sterile electrolyte solution and comprising ions of the radioactive metal and, preferably, the carrier metal and radioactive metal. The concentration of the carrier metal in the solution ranges from about one thousand to about one billion times the concentration of the radioactive metal. The concentration of the radioactive metal in the solution is dependent upon the desired final activity of the device. The metallic device is connected to the negative pole of a power supply using an electrically conductive fastener. Thereafter, the radioactive metal and, preferably, the carrier metal are electroplated onto the surface under conditions effective to provide a homogenous distribution of the radioactive metal in the first layer and to form a first layer having a thickness, preferably, of less than 5 μm, more preferably of less than 1 μ. The amount of radioactive metal in the first layer is adjusted by altering the concentration of radioactive metal in the electrolyte solution, by changing the length of time of the electroplating step, or by altering both parameters.

Preferably, following electroplating of the first layer, the stent is rinsed in a sterile solution, preferably a buffered solution. Then the stent is immersed in a sterile electrolyte solution comprising ions of the barrier metal. The third metal is biocompatible and, preferably, more ductile that the second metal. The metal surface comprising the radioactive layer is connected to the cathode of the power supply using an electrically conductive fastener. Thereafter, a second layer comprising the barrier metal is electroplated onto the first layer comprising the radioactive metal under conditions effective to provide a homogenous second layer having a thickness of less than 5 μm, preferably from about 1–2 μm. After deposition of the second layer, the device is rinsed with a sterile solution to remove any residual material. A procedure comprising multiple rinses is preferred.

The radioactive coating, particularly the multi-layered radioactive coating, may be formed using a plurality of sterile electroplating cells, each of which has a chamber for receiving the device. Preferably the walls which define the chamber are formed from a non-conductive material such as glass, ceramic, or plastic. The materials used to form the cells are also capable of being autoclaved, thereby allowing for sterilization of the cells, and if desired, simultaneous sterilization of the final cell and the device that is contained within the chamber of the final cell. The cell comprises one electrode or a plurality of spaced apart electrodes and an electrically conductive fastener for forming an electrical connection between the negative pole of the power supply and the medical device.

Alternatively, a single sterile electroplating cell is used for all of the electroplating steps. The cell comprises a wall defining a chamber, one or more electrodes attached to the inside wall or embedded in the wall which defines the chamber and positioned so that the electrode is in contact with any solutions placed in the chamber, a conductive fastener for electrically connecting the metallic surface of the medical device to the power supply. The wall also has an inlet port in fluid communication with the chamber of the cell for delivering solutions to the chamber, and an outlet port in fluid communication with the chamber of the cell for removing solutions from the chamber. The size and shape of the chamber depends on the size, shape, number and location of the surfaces to be plated.

Since all of the steps are performed using sterile solutions and sterile equipment, such as for example, sterile electroplating baths, it is contemplated that the medical device will be ready for implantation into the patient following formation of the multilayer coating. Alternatively, a further sterilization step of the device may be performed following the final rinse. Suitable methods of sterilizing the radioactive medical device include, by way of example, autoclaving, dry heat treatment, or ethylene oxide gas sterilization.

The present method for preparing an implantable medical device having a radioactive metallic surface is simple and requires less than 15 minutes to impart radioactivity to the device. Thus, the present method allows preparation of the device in house, i.e., in the hospital where the device is to be implanted. The present method also enables one to reliably deposit a coating comprising a desired amount of radioactivity onto the device. Accordingly, a device tailored to match the needs of the patient can be prepared in the hospital shortly before implantation into the patient. For example, a stent that has a desired length and of the desired type can be prepared with the prescribed radiation dose using the present method either shortly before or even during the initial surgical steps of the angioplasty procedure. In accordance with the present method, it is also possible to prepare a medical device comprising a radioactive coating from several hours up to a week prior to implantation, provided that the time of implantation into the patient is known and the amount of radioactivity is decay corrected.

The present method also permits the application of radioactive rhenium to a metallic surface of the device. The rate of decay of $^{188}$Re is such that 94% of the $^{188}$R decays and emits its beta electron energy within 3 days after deposition of the radioactive rhenium onto the metallic surface of the device. Recent studies have shown that the optimum time for delivering the radiation that aids in preventing restenosis is between 1 hour prior to and 3 days after angioplasty. Moreover, $^{188}$Re can be made easily and economically in house, i.e., within a hospital, using a commercially available $^{188}$W/$^{188}$Re generator. Preparation in house permits hospitals doing angioplasty to produce radioactive stents having the desired amount of radioactivity shortly before or even during the catheterization and stenting procedure. In the case of a device coated with $^{188}$Re, the dose deliverable by the device will be within +/-10% of the dose applied, if the device is implanted within 2 hours after deposition of the radioactive coating thereon.

Radioactive Metallic Medical Device

In another aspect, the present invention provides an implantable, medical device comprising a metallic surface having a radioactive, metallic coating disposed thereon. Preferably, the metal which forms the surface is tantalum, stainless steel, a cobalt-alloy or nitinol. Preferably, the metallic surface is positioned to contact a tissue when the device is implanted in a patient. The radioactive metallic coating comprises a layer comprising a radioactive metal that emits beta-particles and, preferably, low energy gamma rays. Preferably, the radioactive metal is selected from the group consisting of radioactive rhenium (Re) as $^{186}$Re and $^{188}$Re, either combined or alone; radioactive yttrium (Y) as $^{90}$Y; radioactive holmium (Ho) as $^{166}$Ho, radioactive praseodymium (Pr) as $^{142}$Pr, radioactive lanthanum (La) as $^{140}$La, radioactive dysprosium (Dy) as $^{165}$Dy, radioactive samarium (Sm) as $^{153}$Sm, radioactive copper (Cu) as $^{64}$Cu and $^{67}$Cu, or radioactive gold (Au) as $^{198}$Au, and combinations thereof. More preferably, the radioactive metal is $^{188}$Re.

In one embodiment, the radioactive layer further comprises a carrier metal that is capable of adhering to the metallic surface and providing a cohesive layer. Preferably, the carrier metal is less noble than the radioactive metal. More preferably, the second metal is biocompatible. Representative examples of suitable carrier metals include, but are not limited to cobalt, nickel, chromium, manganese, iron, gold, or a combination of these metals.

In another embodiment, a second metallic layer is disposed on the layer comprising the radioactive metal. The second metallic layer comprises a third, barrier metal that is capable of adhering to the radioactive layer and preventing release of the radioactive metal. Preferably, the barrier is biocompatible and, more preferably, more ductile than the carrier metal of the first layer. Preferably, the barrier metal is a noble metal such as gold or platinum, more preferably gold.

The radioactive coating is durable and has radiochemical stability. As used herein a durable coating means that the coating will not crack when the portion of the device on which the radioactive coating is deposited is bent to a 30° angle. Preferably, the coating will not crack when the portion of the device on which the radioactive coating is deposited is bent to a 60° angle. As used herein a coating has radiochemical stability if, following immersion of the surface comprising the radioactive coating in a buffered solution at physiological pH, less than 5% of the radioactive metal is released from the coating over a period of 4 half-lives of the radioisotope. For $^{188}$Re, this means that less than 5% of the radioactive rhenium will be released from the surface within 3 days or 68 hours of immersion of the medical device in a buffered solution at physiological pH. Preferably, the medical device is visible by fluoroscopy when implanted into a living being. A radioactive coating comprising a layer of gold having a thickness of 2 μm is visible by fluoroscopy.

In a preferred embodiment, the medical device is a stent for endovascular use. The radioactive coating is disposed on, at least, the outer surface of the stent. Preferably, the stent is capable of delivering 15 to 20 Gy to the tissue within a distance of 0.5 mm from the radioactive coating. Such stents are delivered to the locus of a stenotic lesion on expandable catheters, such as balloon catheters. Initially, the stent in a first diameter configuration is positioned over the balloon portion of the catheter. After the stent and balloon are delivered to the locus of the stenotic lesion, the balloon is inflated and the stent is expanded from a reduced diameter to an enlarged diameter greater than or equal to the interior of the passageway. Stents made in accordance with the present invention are mechanically stable, and deliver more than 94% of the radiation dose contained within the coating to the target area within a period of from about 12 hours to about 12 days, depending on the radioisotope used. Thus, the stents of the present invention are useful for minimizing or preventing the restenosis that occurs following angioplasty and implantation of a non-radioactive stent. In some cases, the stents of the present invention are also capable of being visualized using fluoroscopy. Thus, migration of the stent from the locus of the stenotic lesion can be monitored when the present stents are used.

In addition to radioactive stents that are implanted into the coronary arteries, the present method may also be used to prepare radioactive stents that are implantable in femeroiliac arteries, the carotid artery, vertebro-basilar arteries, as well as in the interior of other hollow passageways such as for example veins, ureters, urethrae, bronchi, biliary and pancreatic duct systems, the gut, eye ducts, and spermatic and fallopian tubes. The present method may also be used to prepare radioactive arterio-venous shunts, wherein the radioactivity emitted by the shunt will minimize or prevent formation of AV fistulae. The present method may also be used to prepare radioactive metal surfaces on implantable orthopedic devices, bone plates, and screws. Furthermore, metallic implants having a radioactive surface may be used to locally treat tumors, particularly to irradiate incompletely resected tumors following surgery, such as for example, brain tumors. The present method may also be used to prepare radioactive needles or wires used in radiotherapy, more specifically in brachytherapy.

The following examples are for purposes of illustration only and are not intended to limit the scope of the invention as defined in the claims which are appended hereto.

EXAMPLE 1

A multilayered coating comprising a first layer of cobalt and radioactive rhenium (Re) and a second layer of gold was electroplated onto samples of 316 L stainless steel wire (Ethicon, Somerville, N.J.), from which many stents are constructed. The wire samples had a diameter of 0.43 mm. The radioactive rhenium was prepared at the Ohio State University reactor in Columbus, Ohio. 2 mg of $Re_2O_7$ were directly neutron-activated for 1 hour at a neutron flux of $1.5\times10^{13}$ n/cm$^2$/sec, yielding 22.2 MBq $^{186}$Re and 133.2 MBq $^{188}$Re.

All wire samples (n=56) to be electroplated were first rinsed with acetone or hexane to remove oily contaminants, followed by a cathodic acid strike for 8 minutes in a 1 M hydrochloric acid solution containing 0.5 M cobalt chloride in order to activate the surface and provide a seed layer. The current density for the strike was 1075 A/m$^2$. The acetone rinse, the striking, and the plating were all performed by immersing the wire samples sequentially into 1.5mL polystyrene cuvettes (Fischer Scientific, Pittsburgh, Pa.) containing the appropriate solutions. Platinum wires 0.20 mm in diameter (Alfa Aesar, Ward Hill Mass.) were used as anodes and placed vertically along the inside wall of the strike and plating cuvettes. Electroplating was performed using a current-controlled regulated DC power supply (Kenwood, PR18-1.2A, Davis Instruments, Baltimore, Md.).

A radioactive layer was electroplated on the wire by first immersing the wires into a 1 M borate and 0.44 M cobalt plating solution having a pH of 4. Radioactive rhenium in the form of perrhenate was added to the cuvette containing the cobalt plating solution to a final rhenium concentration of 1 mM Re. The amount of radioactivity added was between 4 kBq and 42 MBq. Plating of the first layer was for 2 minutes at a current density of either 400 or 87.5 A/m$^2$. A second layer of gold was disposed on the first layer by immersing the wire in a phosphate buffer, pH 7, containing 0.17 M $K_2HPO_4$, 0.07 M $KH_2PO_4$, and 0.07 M $KAu(CN)_2$ and plating for 5 minutes at a current density of 102 A/m$^2$. The final thickness of the gold layer was 3 μm.

X-ray analysis was performed on selected wire areas by a TN-5500 x-ray microanalysis system (Noran Instruments, Middleton, Wis.) directly under the scanning electron microscope (SEM) JSM-5310 from Jeol, Tokyo, Japan. X-ray analysis was also performed on wires plated with a first layer and not with a second layer. X-ray spectroscopy performed under the scanning electron microscope clearly showed that rhenium was codeposited with the cobalt.

Subsequent to plating, each wire was rinsed three times with 2 mL of phosphate buffer (pH=7.4) and the activity of each of these rinses measured in a gamma counter (AutoLogic, Abbott Laboratories, Abbott Park, Ill.). The plated wires with the higher activity, as well as the remaining plating bath were measured in a radionuclide calibrator (Model 4050, Radcal Corporation, Monrovia, Calif.). The amount of activity deposited was then calculated by dividing the wire activity by the sum of both the plating bath and wire activity, and expressed in percent of the initial activity. Measurements of radioactivity confirmed that rhenium was codeposited with cobalt at a rate of about 0.5% of the total amount of perrhenate present in the solution per minute.

Bending tests were performed on the plated wires. In each case, a reference picture of the wire before bending was taken on the SEM at an accelerating voltage of 15 kV after rinsing in acetone. Each wire was then bent sequentially to approximately 30°, 60°, 90°, 120°, or 150° over a sharp corner of an aluminum block using teflon-coated tweezers. After each bending step, the bent section was inspected by SEM. For purposes of comparison, wires that had been coated with cobalt alone, i.e. the wires lacked an outer gold layer, were also subjected to bending tests.

Bending tests of wires comprising a layer of cobalt and a layer of gold showed that the mechanical properties of the layers depended highly on the cobalt layer thickness. When a wire was plated with cobalt (400 A/m$^2$) for 2 minutes, followed by gold (102 A/m$^2$) for 1 minute, flaking and cracking at 60° and 120° angles were visible with SEM. Reducing the cobalt thickness to 0.3 $\mu$m, by plating at 87.5 A/m$^2$ for 2 minutes, and increasing the gold thickness to 2.6 $\mu$m, by plating at 102 A/m$^2$ for 5 minutes, improved the bending test results. Cracking was not seen at 30°, 60°, or 90°, but some small micro-fractures were distinguishable at 120°.

In contrast, damage was particularly severe in the wires coated with a layer of cobalt and lacking the gold layer, with cracks appearing at an angle of 30° and further widening to broad valleys. Although reducing the electroplating time from 18 minutes to 30 seconds resulted in a much smoother surface, it did not prevent cracking of the single cobalt layer, which was only 0.6 $\mu$m thick, when the wire was bent at an angle of 30°. Thus, a radioactive metallic device lacking a second layer of barrier metal is less preferred.

The adhesion of the coating to the substrate was tested by applying an adhesive tape to the wire, pulling apart the adhesive tape and the wire, and then observing the surface of the wire under the microscope. The results indicated that none of the coating was removed from the surface of wires plated with a first layer of cobalt and rhenium and a second layer of gold.

Additionally, the coated wire surface was scratched first with a fingernail, and then with a razor blade and inspected for damage. No damage to the dual layer coating was observed after scratching with a fingernail. Scratches were observed in the coating when the coated wire was scratched with a razor blade. These results indicate that a coating comprising a first layer of cobalt and rhenium and a second layer of gold has sufficient strength to withstand insertion into and gliding along the catheters used for placement of a stent in a patient as well as the other procedures the stent is normally exposed to prior to implantation in the patient.

Comparative Example A

Wire samples were also subjected to a strike procedure as described in Example 1 but without cobalt chloride followed by directly plating of non-radioactive rhenium from a sulfate bath containing 0.1 M H$_2$SO$_4$ and 0.13 M rhenium. The current density was 1075 A/m$^2$. The bath was kept at room temperature, and the plating time was 10 minutes.

Comparative Example B

Wire samples were also subjected to an 8 minute strike from a hydrochloric acid solution at a pH of less than 1 and a current density of 1075 A/m$^2$. The strike was followed by rhenium plating for 18 minutes from a 1M boric acid electrolyte solution at a pH of about 4, at a current density of 400 A/m$^2$. Both the strike and the rhenium plating were conducted at room temperature.

Results

Plating rhenium metal without a carrier metal onto the steel wires from the sulfate bath as described in comparative Example A yielded no detectable metal on the wire surface. Subjecting the wires to a strike from a hydrochloric acid based strike solution followed by rhenium plating from a boric acid electrolyte as described in Comparative Example B, however, provided a thin layer of dark gray metal on the surface. X-ray analysis indicated that the coating consisted of rhenium. However, the metal could be easily rubbed off. Scanning electron microscopy revealed that the rhenium was plated in streaks along the length of the wire, the streaks consisting of rhenium bubbles approximately 2 $\mu$m in diameter. The current efficiency was very low, yielding only a 0.11 $\mu$m-thick layer deposited per minute of plating time. These results indicate that it is difficult to deposit a homogenous rhenium layer on the metallic surface of a medical device unless a carrier metal is included in the electroplating bath. Accordingly plating from a bath lacking a carrier metal is less preferred.

EXAMPLE 2

A multilayer coating was deposited on wire samples as described in Example 1 except that samples were electroplated with the radioactive rhenium and cobalt for lengths of time, ranging from 1 to 18 minutes. The amount of radioactivity deposited on each wire was measured and the rate of deposit of the radioactive rhenium, i.e. the percent of total radioactivity in the solution electroplated per minute, calculated. The results indicated that the rate of deposit was constant and that the rate of deposit was 0.55% per minute. Thus, the rate of deposit and the total amount of radioactivity in the electroplating solution prior to plating can be used to determine the amount of time required to deposit a desired amount of radioactivity on the metal surface.

EXAMPLE 3

A multilayer coating was deposited on wire samples as described in Example 1 except that that the current density was 300 A/m$^2$ and that rhenium concentrations ranging from 0.05 to 500 $\mu$M were used in the cobalt plating bath. The amount of radioactivity deposited on each sample was measured and the rate of rhenium deposition at different rhenium concentrations calculated. The results indicated that the rate of rhenium deposition was 1.00% per minute from the electroplating solutions containing 0.05 and 5.0 $\mu$M rhenium; 0.88% for the 50 $\mu$M solution; and 0.82% per minute for the 500 $\mu$M rhenium solution. Thus, the deposition rate is relatively constant at the low rhenium concentrations that are used for preparing radioactive stents. Furthermore, the rhenium concentration can be made constant by changing the electroplating solution composition to contain a constant amount of non-radioactive rhenium at a concentration of at least 1000 times higher than the radioactive rhenium concentration, e.g. 50 $\mu$M non-radioactive perrhenate.

EXAMPLE 4

A multilayer coating was deposited on wire samples as described in Example 1 except that the radioactive layer was deposited at current densities ranging from 20 A/m$^2$ to 420

A/m². The amount of radioactivity deposited on each sample was measured and the rate of rhenium deposition at different current densities calculated. The results indicated that the rate of rhenium deposited with cobalt depends on the current density used for electroplating. At 20 A/m², 0.41% of the total rhenium in the electroplating solution was deposited per minute. At 67.5 A/m², the rate of rhenium deposition increased to 0.74% . At increasingly higher current densities, the rate of rhenium deposition increased linearly to a value of 1.10% per minute at a current density of 420 A/m². These results show that using higher plating currents can increase the rate of rhenium deposition.

EXAMPLE 5

A tantalum Wiktor stent having a diameter of 1.5 mm was electroplated under the conditions as described in Example 1 using a total of 29.7 MBq of radioactive rhenium in the plating solution. The plated stent contained radioactive rhenium in a 1.2-μm-thick cobalt layer, with an outer 2-μm layer of gold. The stent was rinsed three times with 3 ml of distilled water each, then mounted on a balloon catheter, and expanded at 2 MPa which is equal to 20 atmospheres, the maximum pressure for inflating this stent. The stent diameter after expansion was about 3.5 mm. The stent was then placed in a 5 mL glass vial filled with 4 mL of phosphate buffer (pH=7.4) and placed in a 37° C. shaking water bath. Serial measurements of both the stent and the buffer were performed daily in the gamma-counter and the released activity calculated. After complete decay of the radioactivity, i.e., 30 days after electroplating, the stent was examined for surface damage using SEM as described above.

The plating of a Wiktor stent for 2 minutes in a 29.7 MBq rhenium solution yielded 492.1 kBq of the activity (or 0.83% per minute) incorporated into a gold-brown coating. No further radioactivity came off after dipping the stent three times in a vial containing distilled water. Further incubation of the stent in phosphate buffer at 37° C. for several days showed a release of about 2% activity during the first 2 days, followed by a further, linear release of ~0.2% radioactivity per day. No cracks were visible under SEM after expanding the stent with the balloon catheter to a pressure of 2 MPa. These results indicate that a radioactive coating formed in accordance with the present method provides a radioactive stent having excellent radiochemical stability and good bending properties. The outer gold layer also provides a stent having good biocompatibility. The outer gold layer also improves stent visibility during fluoroscopy.

EXAMPLE 6

A nitinol wire of 0.25 mm diameter was electroplated under the conditions as described in Example 1 using a total of 5.4 MBq of radioactive rhenium in the plating solution. The wire was rinsed three times with 3 ml of distilled water each, placed in a 4 mL glass vial filled with 4 mL of phosphate buffer (pH=7) and placed in a 37° C. water bath. Serial measurements of both the stent and the buffer were performed daily in the gamma-counter and the released activity calculated.

The results indicated that 98.1 kBq of radioactive rhenium had been deposited on the wire in the form of a gold-brown coating. The calculated rate of deposit was 0.91% per minute. No radioactivity was released from the wire during the washing procedure. A total of 2.0% of the radioactive metal was released by day 4 of incubation in the phosphate buffer at 37° C. Further measurements indicated that 2.4% of the radioactivity had been released by day six of incubation. These results indicate that nitinol, as well as stainless steel and tantalum can be coated with a radioactive coating in accordance with the present method.

While the invention has been described to some degree of particularity, various adaptations and modifications can be made without departing from the scope of the invention as defined in the appended claims.

What is claimed is:

1. A radioactive medical device configured for implantation in an animal, said medical device having a metallic surface and comprising: a radioactive coating disposed on said metallic surface, said radioactive coating comprising a radioactive metal layer comprising:
   (a) a radioactive metal that emits beta particles, said radioactive metal having a half-life of between 2 hours and 7 days and a maximum beta energy of between 0.6 and 2.3 MeV; and
   (b) a non-radioactive carrier metal which is adherent to said metallic surface of said medical device.

2. The medical device of claim 1 wherein said radioactive coating further comprises a barrier metal layer disposed on said radioactive metal layer, said barrier metal layer comprising a non-radioactive, biocompatible barrier metal.

3. The medical device of claim 2 wherein said barrier metal is selected from the group consisting of gold and platinum.

4. The medical device of claim 1 wherein said radioactive coating further comprises a barrier metal layer disposed on said radioactive metal layer, said barrier metal layer comprising a barrier metal, said barrier metal being non-radioactive, biocompatible, and more ductile than said carrier metal.

5. The medical device of claim 4 wherein said radioactive metal is rhenium, said carrier metal is cobalt and said barrier metal is gold.

6. The medical device of claim 1 wherein said radioactive metal also emits low energy gamma rays.

7. The medical device of claim 1 wherein said radioactive metal is selected from the group consisting of rhenium, copper, dysprosium, yttrium, holmium, praseodymium, lanthanum, samarium, gold, and combinations thereof.

8. The medical device of claim 1 wherein said carrier metal is selected from the group consisting of cobalt, nickel, chromium, manganese, iron, gold, and combinations thereof.

9. A radioactive medical device configured for implantation in an animal, wherein said configuration is substantially cylindrical, said medical device having a metallic surface comprising a radioactive coating disposed on said metallic surface, said coating comprising:
   (a) a radioactive metal that emits beta particles, said radioactive metal having a half-life of between 2 hours and 7 days and a maximum beta energy of between 0.6 and 2.3 MeV; and
   (b) a non-radioactive carrier metal which is adherent to said metallic surface of said medical device.

10. The medical device of claim 9 wherein said radioactive coating further comprises a barrier metal layer disposed on said radioactive metal layer, said barrier metal layer comprising a non-radioactive, biocompatible barrier metal.

11. The medical device of claim 9 wherein said radioactive coating further comprises a barrier metal layer disposed on said radioactive metal layer, said barrier metal layer comprising a barrier metal, said barrier metal being non-radioactive, biocompatible, and more ductile than said carrier metal.

12. The medical device of claim 9 wherein said radioactive metal also emits low energy gamma rays.

13. The medical device of claim 9 wherein said radioactive metal is selected from the group consisting of rhenium, copper, dysprosium, yttrium, holmium, praseodymium, lanthanum, samarium, gold, and combinations thereof.

14. The medical device of claim 9 wherein said carrier metal is selected from the group consisting of cobalt, nickel, chromium, manganese, iron, gold, and combinations thereof.

15. The medical device of claim 10 wherein said barrier metal is selected from the group consisting of gold and platinum.

16. The medical device of claim 15 wherein said radioactive metal is rhenium, said carrier metal is cobalt and said barrier metal is gold.

17. A radioactive stent having a metallic surface comprising a radioactive coating disposed on said metallic surface, said coating comprising:

(a) a radioactive metal that emits beta particles, said radioactive metal having a half-life of between 2 hours and 7 days and a maximum beta energy of between 0.6 and 2.3 MeV, and (b) and a non-radioactive carrier metal which is adherent to said metallic surface of said stent; and (c) a barrier metal layer disposed on said radioactive metal layer, said barrier metal layer comprising a barrier metal, said barrier metal being non-radioactive, biocompatible, and more ductile than said carrier metal.

18. The stent of claim 17 wherein said radioactive metal is selected from the group consisting of rhenium, copper, dysprosium, yttrium, holmium, praseodymium, lanthanum, samarium, gold, and combinations thereof.

19. The stent of claim 17 wherein said carrier metal is selected from the group consisting of cobalt, nickel, chromium, manganese, iron, gold, and combinations thereof.

20. The stent of claim 17 wherein said barrier metal is selected from the group consisting of gold and platinum.

21. The stent of claim 17 wherein said radioactive metal is rhenium, said carrier metal is cobalt and said barrier metal is gold.

22. The stent of claim 17 wherein said radioactive layer has preferably a thickness of less than 5 $\mu$m and said barrier metal layer has preferably a thickness of less than 5 $\mu$m.

* * * * *

UNITED STATES PATENT AND TRADEMARK OFFICE
CERTIFICATE OF CORRECTION

PATENT NO. : 6,413,271 B1
DATED : July 2, 2002
INVENTOR(S) : Urs Hafeli, Uziel Landau and Matt C. Warburton It is certified that error appears in the above-identified patent and that said Letters Patent is hereby corrected as shown below:

Column 1,
Line 7, please insert -- The present invention was made with support from National Institutes of Health Grant. The United States Government has certain rights in this invention. --.

Column 2,
Line 15, after "10", please delete "cGy" and insert -- centigray (cGy) --.

Column 7,
Line 63, after "arterio-venous", please insert -- (AV) --.

Column 8,
Line 21 please delete "MBq", and insert -- megabecquerel (MBq) --.

Signed and Sealed this

Twenty-ninth Day of March, 2005

JON W. DUDAS
*Director of the United States Patent and Trademark Office*

UNITED STATES PATENT AND TRADEMARK OFFICE
CERTIFICATE OF CORRECTION

PATENT NO.   : 6,413,271 B1
DATED        : July 2, 2002
INVENTOR(S)  : Urs Hafeli, Uziel Landau and Matt C. Warburton It is certified that error appears in the above-identified patent and that said Letters Patent is hereby corrected as shown below:

<u>Column 4,</u>
Line 4, after "37", please delete "GBq" and insert -- gigabecquerel (GBq) --.

Signed and Sealed this

Seventh Day of June, 2005

JON W. DUDAS
*Director of the United States Patent and Trademark Office*